United States Patent [19]

Gozzo et al.

[11] 4,288,611
[45] Sep. 8, 1981

[54] N-METHYL-CARBAMATES OF 3,5-DIMETHYL-4-(N'-MONOSUBSTITUTED)-AMINOPHENOLS EXERTING AN INSECTICIDAL AND ACARICIDAL ACTION

[75] Inventors: Franco Gozzo; Paride Paolucci, both of S. Donato Milanese; Angelo Longoni, Milan, all of Italy

[73] Assignee: Montedison S.p.A., Milan, Italy

[21] Appl. No.: 151,819

[22] Filed: May 21, 1980

Related U.S. Application Data

[63] Continuation-in-part of Ser. No. 909,304, May 24, 1978, abandoned.

[30] Foreign Application Priority Data

May 26, 1977 [IT] Italy .............................. 24031 A/77

[51] Int. Cl.³ ................ C07C 125/04; C07C 125/067
[52] U.S. Cl. .................................. 560/133; 560/136; 424/300
[58] Field of Search .............................. 560/133, 136

[56] References Cited

U.S. PATENT DOCUMENTS

| | | | |
|---|---|---|---|
| 3,453,316 | 7/1969 | Heiss et al. | 560/136 |
| 3,522,292 | 7/1970 | Nikles | 560/136 |
| 3,819,678 | 6/1974 | Nikles | 560/136 |
| 4,109,011 | 8/1978 | Piccardi et al. | 560/136 |

FOREIGN PATENT DOCUMENTS 2545389  4/1976  Fed. Rep. of Germany ...... 560/136

*Primary Examiner*—Howard T. Mars
*Assistant Examiner*—Frederick W. Pepper
*Attorney, Agent, or Firm*—Morgan, Finnegan, Pine, Foley & Lee

[57] ABSTRACT

There are provided new N-methyl-carbamates of 3,5-dimethyl-4-(N'-monosubstituted)-aminophenols which are characterized by one substituent on the amino group in the 4 position, the substituent being selected from the group consisting of alkenyl, alkynyl, benzyl, cycloalkylmethyl, cyclopropyl-alkyl and dichlorocyclopropylmethyl. These are useful as insecticides and acaricides.

4 Claims, No Drawings

N-METHYL-CARBAMATES OF 3,5-DIMETHYL-4-(N'-MONOSUBSTITUTED)-AMINOPHENOLS EXERTING AN INSECTICIDAL AND ACARICIDAL ACTION

CROSS-REFERENCE TO RELATED APPLICATION

This application is a continuation-in-part of copending application Ser. No. 909,304, filed May 24, 1978 now abandoned.

BACKGROUND OF THE INVENTION

N-methyl-carbamates of 3,5-dimethyl-4-aminophenols-N'-disubstituted are known. For example, German Pat. No. 1,153,012 describes an N-methyl-carbamate of 3,5-dimethyl-4-(N'diallyl)-aminophenol. This is commercially available from Bayer Co., under the trademark "Allyxycarb". It is a known pesticide.

French Pat. No. 2,040,258 describes N-methyl-carbamates of 3,5-dimethyl-4-(N'-disubstituted)-aminophenols which exert a pesticide action.

N-methyl-carbamates of 3,5-dimethyl-4-(N'-monosubstituted)-aminophenol wherein N' is substituted by a dichloro- or trichloro-allyl group, exerting an insecticidal action, are described in Italian patent application No. 22,949 A/75.

DESCRIPTION OF THE INVENTION

There have now been discovered new pesticides which are N-methyl-carbamates of 3,5-dimethyl-4-(N'-monosubstituted)-aminophenols having the general formula:

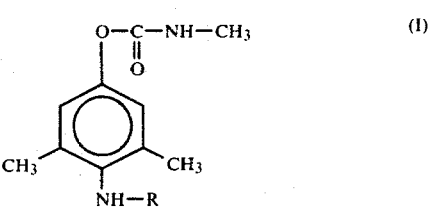

where R is alkenyl, alkynyl, benzyl, cycloalkyl-methyl, cyclopropyl-alkyl, dichlorocyclopropyl-methyl, optionally substituted, exerting a pesticide action superior to that of the known N-methyl-carbamates of 3,5-dimethyl-4-aminophenols N'-substituted.

The compounds of the general formula (I) can be prepared conventionally reacting one mole of halide R-X with an N-methyl-carbamate of 3,5-dimethyl-4-aminophenol. In this way the compounds listed in Table I have been obtained.

TABLE I

| FORMULA | ITEM | M.P. °C. | ANALYSIS Calc. % | Found % |
|---|---|---|---|---|
| OCONHCH₃ / CH₃, CH₃ / NH—CH₂—CH=CH₂ | 1 | oil | C 66.64<br>H 7.74<br>N 11.96 | C 66.27<br>H 7.56<br>N 11.99 |
| OCONH₃ / CH₃, CH₃ / NH—CH₂—C(CH₃)(Cl)(Cl) cyclopropyl | 2 | 135° C. | C 54.39<br>H 6.08<br>N 8.46<br>Cl 21.41 | C 54.19<br>H 5.93<br>N 8.24<br>Cl 20.32 |
| OCONHCH₃ / CH₃, CH₃ / NH—CH₂—C≡CH | 3 | 116° C. | C 67.22<br>H 6.94<br>N 12.06 | C 67.35<br>H 6.99<br>N 11.83 |
| OCONHCH₃ / CH₃, CH₃ / NH—CH₂—C₆H₅ | 4 | 112° C. | C 71.80<br>H 7.09<br>N 9.58 | C 71.58<br>H 6.91<br>N 8.98 |
| OCONHCH₃ / CH₃, CH₃ / NH—CH₂—CH=CH—CH₃ | 5 | oil | C 67.71<br>H 8.12<br>N 11.28 | C 68.74<br>H 7.90<br>N 11.26 |

The activity of the compounds of this invention was compared with that of the compounds of the prior art. The biological action of the compounds of the present invention was tested according to the following methods:

BIOLOGICAL ACTION ON *MACROSIPHUM EUPHORBIAE* (APHIDES)

Potato seedlings cultivated in a pot were infested with adult female aphides and, after a few hours, were sprayed with an aqueous solution of the products to be tested. The mortality percentage was determined 24 hours after the treatment (in untreated seedlings, the mortality is zero).

BIOLOGICAL ACTION ON *PIERIS BRASSICAE* (LEPIDOPTERA)

Cut cauliflower leaves were sprayed with an aqueous dispersion of the products to be tested. After drying, the leaves were infested with 5-day old larvae. The percentage of mortality of the larvae (in untreated leaves, the mortality is zero) was determined 48 hours after the treatment.

BIOLOGICAL ACTION ON *LEPTINOTARSA DECEMLINEATA* (COLEOPTERA)

Potato seedlings cultivated in a pot were infested with 4-day old larvae and sprayed with an aqueous dispersion of the products to be tested. The mortality percent (in untreated seedlings, the mortality is zero) was determined 48 hours after the treatment.

BIOLOGICAL ACTION ON *SPODOPTERA LITTORALIS* (LEPIDOPTERA)

Cut tobacco leaves were sprayed with an aqueous dispersion of the products to be tested. After drying, the leaves were infested with 5-day old larvae. The percentage of mortality of the larvae was determined 48 hours after the treatment (in untreated leaves, the mortality is zero).

BIOLOGICAL ACTION ON ADULT *TETRANYCHUS URTICAE* (Acari)

Small discs of bean leaves were infested with adults of said acarus and successively sprayed with an aqueous dispersion of the products to be tested. The mortality percentage was determined 24 hours after the treatment (in untreated discs, the mortality is zero). The results are recorded in Tables II and III. The mortality is expressed in percent.

TABLE II

| COMPOUND NO. | CONC. % S.Q. | MACROSIPHUM EUPHORBIAE | LEPTINOTARSA DECEMLINEATA | PIERIS BRASSICAE |
|---|---|---|---|---|
| 1 | 0.1 | 100 | 100 | 100 |
|  | .05 | 92 | 100 | 100 |
|  | .01 | 72 | 100 | 60 |
|  | .005 | — | 100 | — |
| 2 | 0.1 | 100 | 100 | 100 |
|  | .05 | 80 | 100 | 100 |
|  | .01 | — | 100 | 100 |
|  | .005 | — | 90 | 100 |
| 3 | 0.1 | 100 | 100 | 100 |
|  | .05 | 80 | 100 | 100 |
|  | .01 | — | 100 | 100 |
|  | .005 | — | 90 | 100 |
| ALLYXYCARB | 0.1 | 41 | 100 | 100 |
|  | .05 | — | 100 | 50 |
|  | .01 | — | 95 | — |
|  | .005 | — | 60 | — |
| 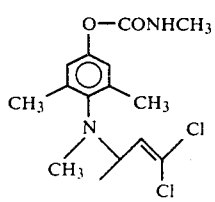 It. Appl. 22949 A/75 | 0.1 | 82 | 100 | 100 |
|  | 0.05 | 15 | 70 | 50 |
|  | 0.01 | 0 | 30 | — |

TABLE III

Mortality % determined at the indicated concentrations on the following Phytophaga.

| COMPOUND | CONC. ‰ S.Q. | SPODOPTERA LITTORALIS | TETRANYCHUS URTICAE (adults) |
|---|---|---|---|
| 1 | 0.1 | 100 | 100 |
|  | .05 | 100 | 45 |
| ALLYXYCARB | 0.1 | 80 | 8 |
|  | .05 | 50 | — |
| (structure) | 0.1 | 97 | 50 |
| It. Pat. App. 22949 A/75 | 0.05 | 55 | — |

It is shown in Tables II and III that the activity exerted by the compounds of the present invention is far greater on *Macrosiphum euphorbiae*, *Pieris brassicae*, *Spodoptera littoralis* and *Tetranychus urticae* than the activity of the prior art aminophenol carbamates.

An overall comparison between the compounds claimed in the present invention and the nearest ones of the prior art having two substituents at the aminophenyl group or a single dichloroallyl group according to U.S. Pat. No. 4,109,011, under the conditions hereinbefore described has been carried out and summarized in the following Table IV.

The compound having two substituents at the amino group bound to the phenyl were 3,5-dimethyl-4-(N-methyl-N-propargylamino)-phenyl-N'-methylcarbamate (described in U.S. Pat. No. 3,522,297 hereinafter called M 10666)

3,5-dimethyl-4-(N-methyl-N-allylamino)-phenyl-N'-methylcarbamate (claimed in U.S. Pat. No. 3,453,316 hereinafter called M 10932)

3,5-dimethyl-4-(N-diallylamino)-phenyl-N'-methylcarbamate (Allylxycarb: Bayer's trademark, hereinafter called M 7482)

3,5-dimethyl-4-(N-dipropargylamino)-phenyl-N'-methylcarbamate (hereinafter called M 9409).

The compound having a single dichloroallyl group according to U.S. Pat. No. 4,109,011 is:

3,5-dimethyl-4-(N-3dichloroallylamino)-phenyl-N'-methylcarbamate (according to U.S. Pat. No. 4,109,011 hereinafter called M 7361).

N-disubstituted ones or than the N'-dichloroallylamino analogues.

The compounds of this invention can be formulated according to known techniques by causing them to be absorbed by suitable powdered materials (earth, diatomaceous earth, etc.), optionally in the presence of surfactants, or they can be prepared as aqueous emulsions or solutions in solvents.

In order to fight infestations of noxious insects belonging to the orders of the Lepidoptera, Hemictera, Coleoptera and Acari, amounts of active principle as such, or in the form of formulations, from 0.005%, upwards, can be sprayed in the habitat, on the food or directly on the insect.

TABLE IV

| | | Mortality % determined at the indicated concentration on the following Phytophaga. | | | | | |
|---|---|---|---|---|---|---|---|
| COMPOUND | FORMULA | CONCEN-TRATION $°/_{oo}$ S.Q. | MACRO-SIPHUM EUPHORBIAE | LEPTI-NOTARSA DECEM-LINEATA | PIERIS BRASS-ICAE | SPODOP-TERA LITTO-RALIS | TETRANYCHUS URTICAE (adults) |
| M 7450 | (structure) | 0.1 | 100 | 100 | 100 | 100 | 100 |
| | | 0.05 | 92 | 100 | 100 | 100 | 45 |
| | | 0.01 | 72 | 100 | 60 | 100 | — |
| | | 0.005 | — | 100 | — | 80 | — |
| M 10.932 | (structure) | 0.1 | 59 | 100 | 100 | 72 | 78 |
| | | 0.05 | — | 92 | 86 | 41 | 23 |
| | | 0.01 | — | 47 | 11 | — | — |
| | | 0.005 | — | 5 | — | — | — |
| M 7482 (ALLYXYCARB) | (structure) | 0.1 | 41 | 100 | 100 | 80 | 8 |
| | | 0.05 | — | 100 | 50 | 50 | — |
| | | 0.01 | — | 95 | — | — | — |
| | | 0.005 | — | 60 | — | — | — |
| M 8927 | (structure) | 0.1 | 100 | 100 | 100 | 100 | 100 |
| | | 0.05 | 80 | 100 | 100 | 100 | 40 |
| | | 0.01 | 60 | 100 | 100 | 100 | 23 |
| | | 0.005 | — | 90 | 100 | 80 | — |
| M 10666 | (structure) | 0.1 | 62 | 100 | 100 | 100 | 83 |
| | | 0.05 | — | 100 | 100 | 55 | — |
| | | 0.01 | — | 41 | 89 | — | — |
| | | 0.005 | — | — | 27 | — | — |
| M 9409 | (structure) | 0.1 | 77 | 100 | 100 | 100 | 59 |
| | | 0.05 | — | 100 | 80 | 80 | — |
| | | 0.01 | — | 166 | 45 | 38 | — |
| | | 0.005 | — | 5 | — | — | — |
| M 7361 | (structure) | 0.1 | 50 | 100 | 100 | 100 | 27 |
| | | 0.05 | — | 20 | 50 | 50 | — |
| | | 0.01 | — | — | — | — | — |
| | | 0.005 | — | — | — | — | — |

From the table one can assume that the described N-methyl carbamates of 3,5-dimethyl-4-(N'-monosubstituted) aminophenols are far more active than the

DESCRIPTION OF THE SPECIFIC EMBODIMENTS

The following examples are given to better illustrate the present invention.

EXAMPLE 1

This example illustrates the preparation of N-methyl-carbamate of 3,5-dimethyl-4-(N'allylamino)phenol.

97.1 g of N-methyl-carbamate of 3,5-dimethyl-4-aminophenol were dissolved in 290 ml of N,N-dimethylformamide. 29 ml of water and 84 g of sodium bicarbonate were added to the solution, whereupon, under intense stirring, 60 g of allyl bromide dissolved in 60 ml of N,N-dimethylformamide were dropped thereinto. At the conclusion of such addition, the reaction mixture was kept under stirring at room temperature for 3 hours, then it was poured into 1,050 ml of water and it was extracted three times with 350 ml of benzol. The organic extracts were gathered, washed with water, anhydrified on $Na_2SO_4$ and evaporated at 40° C. at 15 Torr, until obtaining a residue weighing 74.5 g.

$C_{13}H_{18}N_2O_2$ analysis: $C_{calc.}$: 66.64%; $C_{found}$: 66.27%;
$H_{calc.}$: 7.74%; $H_{found}$: 7.56%;
$N_{calc.}$: 11.96%; $H_{found}$: 11.99%.

EXAMPLE 2

This example illustrates the preparation of N-methyl-carbamate of 3,5-dimethyl-4-(N'-2,2-dichloro-1-methyl-cyclopropyl-methylamino)-phenol.

A solution containing 4.7 g of N-methyl-carbamate of 3,5-dimethyl-4-aminophenol and 5.3 g of 1,1-dichloro-2-methyl-2-iodomethyl-cyclopropane in 25 ml of N,N-dimethylformamide was heated to 100° C. for 8 hours, under stirring. After this period of time, the reaction mixture was cooled to 20° C. and 2 g of triethylamine were added thereto; it was stirred for 30 minutes, whereupon 80 ml of water and 80 ml of benzol were added. The aqueous phase, after separation from the organic phase, was extracted again with 80 ml of benzol, the benzene extracts were gathered and washed with water, then they were treated with a 1% solution of HCl to a pH=4 and, finally, washed again with water. The resulting organic phase was anhydrified on $Na_2SO_4$ and the solvent was evaporated at 50° C. and at 15 Torr. The oily residue, after treatment with n-hexane, provided a solid product having a melting point of 135° C.

$C_{15}H_{20}Cl_2N_2O_2$ analysis: $C_{calc.}$: 54.39%; $C_{found}$: 54.19%;
$H_{calc.}$: 6.08%; $H_{found}$: 5.93%;
$N_{calc.}$: 8.46%; $N_{found}$: 8.24%;
$Cl_{calc.}$: 21.41%; $Cl_{found}$: 20.32%.

We claim:
1. N-methyl-carbamate of 3,5-dimethyl-4-(N'-allylamino)phenol.
2. N-methyl-carbamate of 3,5-dimethyl-4-(N'-propargylamino)phenol.
3. N-methyl-carbamate of 3,5-dimethyl-4-(N'-2,2-dichloro-1-methyl-cyclopropyl-methyl-amino)phenol.
4. N-methyl-carbamate of 3,5-dimethyl-4-(N'-benzylamino)phenol.

* * * * *